United States Patent [19]

Beard et al.

[11] 4,111,999

[45] Sep. 5, 1978

[54] CLEAVAGE OF SILYLATED CARBORANES AND METHOD FOR PREPARING META-CARBORANE EMPLOYING SAME

[75] Inventors: Charles D. Beard, Yorktown Heights; Robert B. Moffitt, III, Ossining, both of N.Y.

[73] Assignee: Union Carbide Corporation, New York, N.Y.

[21] Appl. No.: 865,893

[22] Filed: Dec. 30, 1977

[51] Int. Cl.$^2$ .................................................. C07F 5/02
[52] U.S. Cl. ......................... 260/606.5 B; 260/37 R; 260/448.2 E; 528/5
[58] Field of Search ................ 260/606.5 B, 448.2 E, 260/37 R, 46.5 E

[56] References Cited

U.S. PATENT DOCUMENTS

| | | | |
|---|---|---|---|
| 3,366,656 | 1/1968 | Papetti | 260/448.2 E |
| 3,388,090 | 6/1968 | Heying et al. | 260/37 R |
| 3,388,091 | 6/1968 | Heying et al. | 260/37 R |
| 3,388,092 | 6/1968 | Heying et al. | 260/37 R |
| 3,388,093 | 6/1968 | Heying et al. | 260/37 R |
| 3,440,265 | 4/1969 | Heying et al. | 260/606.5 B X |
| 3,457,222 | 7/1969 | Papetti | 260/46.5 E |
| 3,457,223 | 7/1969 | Papetti | 260/46.5 E |
| 3,542,730 | 11/1970 | Papetti et al. | 260/46.5 E |
| 3,562,212 | 2/1971 | Kongpricha et al. | 260/46.5 E |
| 3,637,589 | 1/1972 | Kwasnik et al. | 260/46.5 E |

*Primary Examiner*—Paul F. Shaver
*Attorney, Agent, or Firm*—William Raymond Moran

[57] ABSTRACT

A highly selective method is disclosed for cleaving carboranyl carbon-silicon bonds which comprises contacting either silylated monomeric carboranes or polymers thereof with a nucleophilic cleavage agent and, if desired, in the presence of a protic reagent and recovering the carborane cage intact. This technique is employed in a method for producing the useful meta-carborane in bulk which includes the steps of isomerizing a silylated derivative of ortho-carborane using known techniques to produce the corresponding meta-carborane derivative and then cleaving the carboranyl carbon-silicon bond to form meta-carborane.

21 Claims, No Drawings

CLEAVAGE OF SILYLATED CARBORANES AND METHOD FOR PREPARING META-CARBORANE EMPLOYING SAME

BACKGROUND

This invention relates to a method for the cleavage of carboranyl carbon-silicon bonds in compounds and polymers containing same, and in addition, to a method for preparing meta-carborane using this technique.

Ortho-Carborane, of the empirical formula $C_2B_{10}H_{12}$, has an icosahedral structure and was the first icosahedral carborane discovered and prepared in quantity. Subsequently, methods were developed for isomerizing the ortho derivative to the meta-and para-isomers. For example, ortho-carborane may be rearranged or isomerized to meta-carborane in a hot tube flow process at high temperatures (i.e., 600° C) involving short residence times. See S. Papetti, et al, *Industrial Engineering Chemical Product Research and Development*, 5, 334 (1966). At these temperatures, carborane vapors may burn or explode if allowed to contact air and hence such a process is not attractive for industrial operation.

Another process is known for isomerizing carboranes in bulk and is disclosed in U.S. Pat. No. 3,440,265. The process involves the thermal rearrangement of large silyl group-substituted ortho-carboranes to the metal-isomer at significantly lower temperatures than the prior technique. In contrast to the earlier flow process, this bulk isomerization occurs readily at the reflux temperature and can be performed using conventional laboratory equipment. Furthermore, the method is adaptable to large-scale industrial production.

The metal-isomer has become increasingly important as the key ingredient of high performance metal-carborane-siloxane polymers. Such polymers have excellent high temperature characteristics and can be prepared by methods known in the art. For example, linear, high molecular weight carborane-siloxane polymers and methods for their preparation are disclosed in commonly-assigned, copending U.S. Pat. Application Ser. No. 770,509, filed Feb. 22, 1977. These polymers may be compounded with suitable fillers and additives and fabricated into cured elastomeric articles. The excellent high temperature properties of such elastomers make them especially useful for a wide variety of applications, such as gaskets, seals, wire and cable insulation, and the like. Although carborane-siloxane polymers have excellent high temperature and other high performance characteristics, they are extremely expensive to produce. Hence, it would be an advantage to be able to reclaim the carborane portion from scrap, off-grade or otherwise used-up polymer, and also to recover or regenerate carborane monomer by-products used in forming the carborane-siloxane polymers.

It is known in the art that the carborane icosahedral structure is subject to attack by strong bases. See, for example, Papetti, et al, *Inorganic Chemistry*, 3 1444 (1964) which discloses without detailed explanation that some cyclic silylated carboranes are cleaved. In addition, Schwartz, et al, *Inorganic Chemistry*, 4, 661-4 (1955) indicate that a very labile diethoxysilylated carborane is cleaved under acidic or basic conditions not specified.

The present invention provides a technique for highly selectively cleaving carboranyl carbon-silicon bonds in monomeric silylated carboranes and carborane polymers. The method taught herein is highly selective in that the carborane cage contained in these materials may be recovered intact which is highly advantageous due to the expensive nature of the materials involved. Further, this novel technique may be employed in a process for the formation of metal-carborane in bulk when used in combination with known techniques. This represents a significant advance since this method for preparing meta-carborane in high yield in bulk may be practiced on a large-scale, industrial level.

SUMMARY OF THE INVENTION

The invention is a process for selectively cleaving carboranyl carbon-silicon bonds in monomeric silylated carboranes and carborane-siloxane polymers which comprises contacting the monomer and polymer with a nucleophilic cleavage agent to cleave the carboranyl carbon-silicon bond and, if desired, in the presence of a protic reagent and recovering the carbonane cage intact. The invention also involves a method for producing meta-carborane, m-$C_2B_{10}H_{12}$, in bulk from ortho-carborane derivatives employing this cleavage process, which method includes the steps of isomerizing the ortho-carborane derivative using known techniques to produce the corresponding meta-carborane derivative, followed by cleaving the carboranyl carbon-silicon bond thereof and recovering intact the meta-carborane cage.

The present invention is advantageous in that it permits the rare and expensive carborane portion of scrap, offgrade or used-up polymer, even cross-linked polymer, to be reclaimed and recycled in the synthesis of fresh monomer and polymer. Likewise, carborane by-products generated during production of the carborane monomers may also be recovered and recycled. In effect, the ability to recover and recycle the carborane cage intact enables one to achieve a substantially total conversion to carborane-siloxane polymer from carborane monomer. The improved method for producing metal-carborane in bulk is readily adaptable to large-scale industrial operation and avoids the difficulties of some prior art techniques.

DETAILED DESCRIPTION

The present invention may be employed to cleave carboranyl carbon-silicon bonds in various substrates, including carborane-siloxane polymers and mono- or di-silylated carborane monomers, and derivatives thereof. Broadly, the cleavage process of the invention may be employed with any carborane substrate which has one or more carboranyl carbon-silicon bonds, although for ease of description, the invention will be described by reference to its preferred embodiments. For example, a carborane-siloxane polymer substrate may have a repeating unit represented by the following formula:

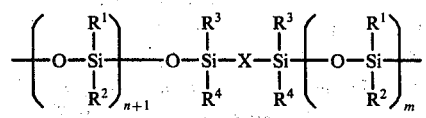

wherein $R^1$ and $R^2$, which may be the same or different, each represents hydrogen or a group containing up to 14 carbon atoms and selected from the group consisting of alkyl, alkenyl, cycloalkyl, aryl, alkaryl, aralkyl, alkoxyaryl, haloalkyl, haloaryl, cyanoalkyl, and pyridinyl; $R^3$ and $R^4$, which may be the same or different, each represents hydrogen or a group containing up to 14 carbon atoms and selected from the group consisting of alkyl, alkenyl, aryl, alkaryl, alkoxy, alkoxyalkyl, haloalkyl, haloaryl and cyanoalkyl; X represents a divalent radical derived from a carborane which may be 1,7-decacarborane, also known as 1,7-dicarba-closo-dodecaborane (12) and meta-carborane; 1,2-decacarborane, also known as 1,2-dicarba-closo-dodecaborane (12) and ortho-carborane; 1,12-decacarborane, also known as 1,12 -dicarba-closo-dodecaborane (12) and para-carborane; 1,10-octacarborane; 1,6-octacarborane; 2,4-penta-carborane; 1,6-tetracarborane; 9-alkyl-1,7-decacarborane, 9,10-dialkyl-1,7-decacarborane; 2-alkyl-1-12-decacarborane; 1,7-decacarborane; decachloro-1,12,-decacarborane; octachloro-1,10-octacarborane; decafluoro-1,7-decacarborane; decafluoro-1,12-decacarborane; octafluoro-1,10-octacarborane, or mixtures thereof; and $m$ and $n$ individually have a value of from 0 to 4. For the purpose of this application the term "decacarborane" is employed to denote "dicarbo-closo-dodecaborane." The molecular weight of these polymers is not critical and may vary over a wide range depending on the properties desired. As those skilled in the art realize, the elastomeric characteristics of these polymers generally improve with increased molecular weight but their processability suffers with such increases. Therefore, it may be desirable to provide a relatively lower molecular weight material, with adequate properties, in order to achieve good processability.

The aforementioned commonly-assigned, copending U.S. Application Ser. No. 770,509, filed Feb. 27, 1977, discloses several methods for the preparation of linear polymers of the above type having a weight average molecular weight of up to about 150,000 and higher. Specifically, and as set forth therein, linear carborane-siloxane polymers may be formed by the condensation of silyl diamines or $\alpha,\omega$-diaminosiloxanes with carborane disilanols. In a second embodiment, such linear polymers are also prepared by the condensation of ureidosilanes or $\alpha,\omega$-ureidosiloxanes with carborane disilanols. In a further embodiment, carborane disilanols can be condensed with silyl bis-carbamates or $\alpha,\omega$-carbamoylsiloxanes to form such carboranesiloxane polymers.

Specific examples of such polymers are the linear $D_2$-siloxane polymers of the above formula where $m$ is $m=0$ and $n=1$ , $R^1$, $R^3$ and $R^4$ are all methyl and $R^1$ is phenyl, vinyl or trifluoropropyl or mixtures thereof, and X is meta-carboranyl, $-C_2B_{10}H_{10}-$, and which have a molecular weight of about 150,000 (weight average) and are compounds of Union Carbide Corporation under the Trademark UCARSIL.

Illustrative of the $R^1$-$R^4$ groups as herein before defined are such groups as methyl, ethyl, n-propyl, n-butyl, n-pentyl, n-hexyl, butenyl, hexenyl, cyclopentyl, cyclohexyl, phenyl, benzyl, o-m-, or p-chlorophenyl, o-,m- or p-methylphenyl, o-,m-, or p-methoxyphenyl, 3,3,3-trifluoropropyl, cyanomethyl, pyridinyl and the like.

The mono- and di-silylated carborane monomers which may be treated by the method of the invention may be represented by the formula:

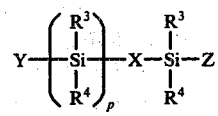

wherein X, $R^3$ and $R^4$ are as described above; $p$ is 0 or 1; Y and Z, which may be the same or different, each represents a hydroxy group and derivatives such as alkoxy or aryloxy, a halogen atom, a hydrogen atom or a group containing up to about 14 carbon atoms, such as alkyl, particularly methyl, aryl, cycloalkyl and the like. Specific examples of mono-silylated carboranes ($p=0$) are trimethylsilyl - o-,m- ,m- or p-carborane, dimethylphenylsilyl- o-,m- or p-carborane or dimethylethylsilyl- o-,m- or p-carborane and the like.

Specific examples of the di-silylated carboranes ($p=1$) are bis(hydroxydimethylsilyl) - o-,m- or p-carborane, bis(trimethylsilyl) - o-,m- or p-carborane, bis(-dimethylchlorosilyl) - o-,m- or p-carborane, bis(dimethylphenylsilyl)-o-,m- or p-carborane, bis(dimethylethylsilyl) - o, m or p-carborane and the like.

The cleavage process of the invention involves the steps of contacting the substrate containing the carboranyl carbon-silicon bond with the nucleophilic cleavage agent and, (if necessary or desired) in the presence of a protic reagent and recovering the resulting carborane cage intact. It is preferred to dissolve or suspend the substrate in a suitable solvent, such as an organic solvent inert to the cleavage reaction. Typical solvents include such inert organic solvents as tetrahydrofuran, benzene, hexane, diethylether and the like, with tetrahydrofuran being the preferred organic solvent. Since it is advantageous to remove any solvent prior to recovery and purification of the carborane produced in the reaction, a low boiling solvent is preferred.

The nucleophilic cleaving agent may be characterized as an electron-rich material such as a base which is capable of cleaving the carboranyl carbon-silicon bond without destroying the integrity of the carborane cage itself. For example, the nucleophile may be a halide (e.g., a fluoride), hydroxide, cyanide, azide, borohydride, amide, alkoxide, mercaptide or acylate of an alkali metal or alkaline earth metal. the preferred nucleophilic agents are potassium fluoride and potassium hydroxide although other similar materials can be employed such as the above. Most of the foregoing are relatively strong nucleophiles and may be employed in the present invention. The particular nucleophile employed is not critical, as long as the integrity of the carborane cage is retained.

As an example of the chemistry involved in the cleavage reaction, the following equations (1), (2) and (3) are provided to illustrate the cleavage of a carboranyl carbon-silicon bond in a carborane-siloxane polymer using a nucleophilic agent such as potassium fluoride:

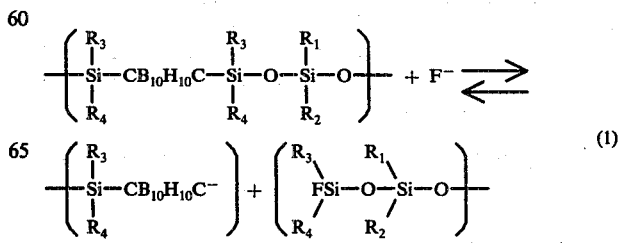

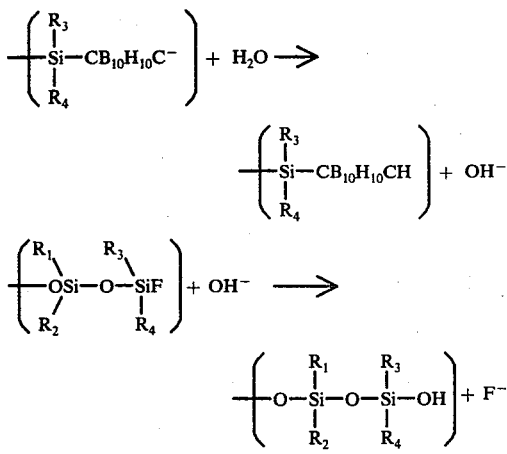

-continued $$\left\{ \begin{array}{c} R_3 \\ | \\ -Si-CB_{10}H_{10}C^- \\ | \\ R_4 \end{array} \right\} + H_2O \longrightarrow \quad (2)$$

$$\left\{ \begin{array}{c} R_3 \\ | \\ -Si-CB_{10}H_{10}CH \\ | \\ R_4 \end{array} \right\} + OH^-$$

$$\left\{ \begin{array}{c} R_1 \quad R_3 \\ \backslash \quad \backslash \\ -OSi-O-SiF \\ / \quad | \\ R_2 \quad R_4 \end{array} \right\} + OH^- \longrightarrow \quad (3)$$

$$\left\{ \begin{array}{c} R_1 \quad R_3 \\ | \quad | \\ -O-Si-O-Si-OH \\ | \quad | \\ R_2 \quad R_4 \end{array} \right\} + F^-$$

As illustrated by the foregoing equations, the polymer chain is selectively cleaved and the nucleophilic agent is regenerated. The net result with successive cleavages is that the carborane cage is liberated without being itself degraded. As shown in equation (3), nucleophiles are preferred whose bonds to silicon are easily displaced as shown, since they are required only in small, catalytic amounts. In view of the fact that the nucleophilic agent is regenerated, it may be employed in catalytic rather than stoichiometric amounts, as discussed below.

The amount of the nucleophilic agent employed may vary widely. For example, when potassium fluoride is employed, it may be employed in concentrations of about 0.01 to about 50% by weight, based on the weight of the substrate, with the range being from about 5 to about 15% by weight for polymeric substrates and from about 0.01 to about 5% by weight for monomeric substrates. Similarly, when the nucleophile is potassium hydroxide, the concentration may range from about 2 to about 15% by weight, based on the weight of the substrate, preferably from about 8 to about 12% by weight.

The temperature and time of reaction are not especially critical. It has been found that the cleavage process is best carried out for moderate times under mild conditions. The temperature and time will of course vary depending upon the substrate, and the nucleophile and its strength, with the use of a very strong nucleophile requiring less time at a lower temperature. The preferred reaction time at room temperature is about 12–24 hours although the time may in fact vary from about 8 to about 48 hours. While ambient temperatures are preferred as an energy conservation measure, the reaction may be carried out at any temperature between about −10° to about 70° C, preferably from about 15° to about 30° C. Those skilled in the art will realize that longer reaction times are required at lower temperatures with, conversely, shorter times required at higher temperatures.

Since the monomeric and polymeric substrates treated by the process of the invention are essentially non-polar in nature, and since the polar cleavage nucleophiles are preferably used in aqueous solution, it is desirable and therefore preferred to also employ a rate-enhancing agent to aid in transporting the nucleophile to the substrate for reaction therewith. Such rate-enhancing agents may be, for example, a phase transfer catalyst or a crown ether. The phase transfer catalyst can be a cationic, anionic or nonionic surface active agent. A suitable phase transfer catalyst is a methyltrialkylammonium chloride wherein the alkyl groups have from 8 to 10 carbon atoms. Such a product is available from the Ashland Chemical Company under the trademark Adogen 464. This particular material may be employed in an amount of about 0.5% by weight, based on the weight of the substrate. Cationic phase transfer catalysts are generally ammonium or phosphonium salts bearing medium to long chain alkyl or aralkyl substituents containing about 4 to about 8 carbon atoms. These lipophilic groups help transport the polar nucleophilic cleavage agent into the organic phase of the substrate to thereby assist the reaction. Another example of an effective phase transfer catalyst is triethylbenzylammonium chloride.

The addition of the phase transfer catalyst might cause a rise in temperature necessitating the use of a cooling bath to maintain the temperature of reaction within the preferred range of about 15° to about 30° C.

The other rate enhancing agent useful in nonaqueous solvent media may be crown ether which enhances the basicity and/or nucleophilicity of the nucleophilic agent by coordinating the cation very tightly and freeing the anion to react and cleave the carboranyl carbon-silicon bond. The amount employed may be catalytic or greater. Crown ethers are known and are commercially available materials. See, for example, an article by G. W. Gokel and H. Dupont Durst in *Synthesis* 1976, 168 entitled, "Principles and Synthetic Applications in Crown Ether Chemistry". As disclosed therein, the crown ethers are effective complexing agents and they may be therefore employed in the present invention for this purpose to assist in bringing the nucleophilic agent into the organic phase occupied by the substrate. An example of a useful crown ether is 18-crown-6.

The amount and type of the rate enhancer employed in the practice of the present invention may vary as described above. When the process is conducted in aqueous solution, a cationic, anionic or nonionic surface active agent may be employed, whereas in anhydrous organic solution, a material such as a crown ether may be employed. The amount employed depends to an extent upon the strength of the nucleophile as is apparent to those skilled in the art.

The remaining reaction conditions are not critical, and any conventional equipment can be employed in the practice of the present invention. In practice, the substrate is dissolved or suspended in a suitable solvent to which is added the nucleophilic agent. After maintaining suitable agitation if necessary for a period of time, the intact carborane cage may be separated from the reaction mixture by known methods and recovered.

The substrate treated by the process of the present invention can be in any physical form, for example, it may be a simple liquid or solid monomeric silylated carborane resulting from, for example, the synthesis of a disilanol monomer starting from an unsubstituted carborane cage. Alternatively, the substrate may be a soluble polycondensation of oligomeric or high molecular weight. Another substrate is a commercial carborane-siloxane elastomeric polymer, and still others include cross-linked and/or compounded carborane-siloxane materials containing, for example, extending agents such as silica or pigments such as carbon black or ferric oxides. The substrate may be a raw polymer, a compounded mass or a shaped article such as O-rings, gaskets and the like. The substrates described above may be used alone or mixed together. If a shaped material such as a gasket is used as the substrate, it is preferably chopped or ground as fine as possible before being treated by the method of the invention.

The cleavage reaction produces a carboranyl anion. Normally, although it is not necessary, one would continue the reaction by adding or having added a source of proton hydrogen such as water and/or an alcohol to form the corresponding carborane material. Alternatively, the reaction may be continued by adding a suitable agent such as alkyl halide to form, in this case, an alkylated carborane. The invention resides in cleaving the carboranyl carbon-silicon bond in the substrate and it is not necessary that the carborane itself be formed or isolated. Any proton source may be employed in the practice of the invention. Exemplary proton sources are water, methanol, ethanol, ethylene glycol, n-propanol or glycerol. Since the proton source would be used up, the economics of the reaction plus the ease of separation of by-products would affect the choice of proton source to an extent. For example, alcohols lead to -Si-OR derivatives, whereas water gives simple siloxane polymer as well as cyclic trimers.

As stated above, the desired carborane may be recovered by conventional means. For example, the carborane may be extracted from the reaction mixture with a volatile solvent followed by separating the organic and aqueous layers, drying the organic layer and evaporating the organic solvent to recover the carborane. Evaporation of the solvent yields a crude reaction mixture from which the carborane can be purified by vacuum sublimation to achieve a yield which is normally greater than 90% by weight of the carborane contained in the substrate.

In another aspect of the present invention, the above described process for cleaving carboranyl carbon-silicon bonds can be employed in a pactical, large scale method for producing meta-carborane in bulk, in combination with known processes for isomerizing ortho-carboranes to the more useful meta-carboranes. Essentially, this technique comprises the steps of isomerizing a derivative of ortho-carborane by any conventional technique to the corresponding meta-carborane derivative and, after isomerization, cleaving the meta-compound to yield meta-carborane in high yield. The isomerization can be conducted using any conventional technique, preferably that disclosed in U.S. Pat. No. 3,440,265. As described therein, silylated derivatives of ortho-carborane may be synthesized, such as the trimethylsilyl, chlorodimethylsilyl, and the like. The preferred derivative is trimethylsilyl since it is less air and water sensitive than other similar derivatives.

As disclosed in said patent, the isomerization process comprises heating the ortho-carborane derivative at a temperature of from about 290° to 375° C. Although carried out conveniently at atmospheric pressure, if desired, pressures as high as about 100 psi can be employed. It is further stated that preferably, for those ortho-carborane derivatives having boiling points between about 290° and 375° C, the isomerization reaction is conducted at reflux temperature. The time of the reaction will vary with the temperature and with the particular starting material and other reaction conditions employed, and generally will be between about 0.25 to 30 hours or more. As stated above, the preferred ortho-carborane derivatives employed in the isomerization process are the trialkylsilyl ortho-carboranes, such as trimethylsilyl-ortho-carboranes.

The above-described isomerization process is merely exemplary of the conversion of the ortho-carborane derivative to the meta-carborane derivative. Any technique can be employed to convert the ortho-carborane derivative into the corresponding meta-carborane derivative, followed by treatment with the nucleophilic cleaving agent of the invention to produce the corresponding meta-carborane itself. Although the preferred isomerization technique is as described in said U.S. Pat. No. 3,440,265, the present invention is not to be limited thereby but rather only by the scope of the claims appended hereto.

The cleavage process of the present invention provides an unexpectedly advantageous procedure for producing meta-carboranes. Considering the fact that certain strong bases may attack and degrade the icosahedral structure of certain carboranes, the process of the invention for the selective cleavage of the carboranyl carbon-silicon bonds of various carborane substrates without harming the integrity of the carborane cage is an unexpected discovery.

EXAMPLE 1

To a 500 ml, three-necked flask equipped with a mechanical stirrer, a nitrogen inlet, and a thermometer were added a carborane-siloxane polymer available from Olin Mathieson Chemical Corporation under the Trademark Dexsil 202 (10 g) and tetrahydrofuran (100 ml). A solution of potassium fluoride (1 g of KF·2H$_2$O dissolved in 50 ml of water) was added in a single portion. With stirring and cooling in an ice-water bath, one drop of a methyltrialkylammonium chloride surface-active agent available from Ashland Chemical Company under the Trademark Adogen 464 was added. The cooling bath was removed and the two-phase reaction mixture was stirred for 16 hours at ambient temperature. The reaction mixture was transferred to a separatory funnel and the layers were separated. The organic layer was washed with saturated sodium chloride solution (100 ml), dried (over MgSO$_4$), and filtered. Evaporation of the solvent gave a viscous residue. Vacuum sublimation yielded 2.79 g (93% of theory) of m-carborane which was identified by comparison of the nmr and ir spectra, and glpc retention time with those of an authentic sample. The non-volatile sublimation residue appeared to be a non-boron containing silicone polymer.

EXAMPLE 2

122 g of a cured and compounded m-carborane-siloxane polymer, a compound of Union Carbide Corporation under the Trademark UCARSIL, containing silica (30 phr) and Fe$_2$O$_3$(2.5 phr) was cut into small pieces (about 1 cm$^2$). A 200 ml, 3-necked flask was equipped with a mechanical stirrer and a thermometer and the UCARSIL and 500 ml of tetrahydrofuran were added to the reaction flask. The resulting suspension was stirred while a solution of potassium fluoride (35 g of KF·2H$_2$O in 500 ml of water) was added in a single portion. With stirring and cooling in an ice bath, two drops of Adogen 464 were added. The cooling bath was removed and the reaction mixture was stirred at ambient temperature for 24 hours. The layers were separated and the organic layer was washed with saturated sodium chloride solution (500 ml), dried (over MgSO$_4$), and filtered. Evaporation of the solvent gave a viscous residue. Vacuum sublimation yielded 42 g of m-carborane.

EXAMPLE 3

A 5000-ml three-necked flask was equipped with a mechanical stirrer, thermometer, reflux condenser, addition funnel, and nitrogen inlets. All of the apparatus was oven dried and allowed to cool under a nitrogen atmosphere. o-carborane (136.8g, 0.95 mol) and 1500 ml of anhydrous diethyl ether were added to the reaction vessel. n-Butyl lithium (2.0 mol, 2.4M in hexane, 10% excess) was placed in the addition funnel and added dropwise over four hours. The internal temperature was maintained in the range 0°–10° C by cooling the flask in an ice bath. After completion of the addition, the cooling bath was removed and the reaction mixture was stirred at ambient temperature for 15 hours. Trimethylchlorosilane (217.4 g, 2.0 mol) was placed in the addition funnel and added rapidly (over 15 sec) with cooling to −78° C (Dry Ice-acetone bath). The reaction mixture was stirred at −78° C for 3 hours, at 25° C. for three hours, at reflux for 2 hours, and then poured into 2000 ml of ice water. The organic layer was washed with saturated sodium chloride solution, dried (over MgSO$_4$), and filtered. Evaporation of the solvent gave a crude solid which was recrystallized from heptane yielding 235.5 g (86%) of bis-trimethylsilyl-o-carborane, m.p. 134°–136° C (literature m.p. 141°–142° C). The product was also characterized by nmr and ir.

EXAMPLE 4

A 250 ml, modified Claisen flask was equipped with a magnetic stirrer, a heating mantle, a thermometer and a nitrogen inlet. A mercury bubbler containing 250 mm of mercury was used which gave an internal pressure of approximately 1.35 atmospheres. 100 g (0.347 mol) of bis-trimethylsilyl-o-carborane was placed in the reaction flask under nitrogen. The material was heated at reflux for 20 hours. The reflux temperature was in the range 320°–360° C.

The reaction product solidified when cooled to room temperature. Distillation of the product gave 99 g (99%) of bis-trimethylsilyl-m-carborane bp 80°–82° (0.07 mm), mp 44°–46° C. Glpc analysis indicated that the product consisted of 98.7% of the meta isomer and 1.3% of the ortho isomer. The product was characterized by nmr and ir.

EXAMPLE 5

A 5000 ml, three-necked flask was equipped with a mechanical stirrer, thermometer, reflux condenser, addition funnel, and a nitrogen inlet. A solution of potassium fluoride (12 g, anhydrous) in dry methanol (1000 ml) was placed in the reaction flask and cooled in an ice-water bath. A solution of bis-trimethylsilyl-m-carborane (824g, 2.9 mol) in tetrahydrofuran (2000 ml) was added dropwise with stirring. The internal temperature was maintained in the range 0°–10° C. After completion of the addition (over 4 hrs), the cooling bath was removed and the reaction mixture was stirred for 15 hrs at ambient temperature. The solvents including the by-product trimethylmethoxysilane were removed in vacuo. Water (1000 ml) was added, and the product was extracted with diethyl ether (2000 ml). The ethereal solution of the product was washed with a saturated sodium chloride solution, dried over MgSO$_4$, and filtered. The solvent was removed on a rotary evaporator and the residue was vacuum sublimed giving 397 g (96%) of m-carborane.

EXAMPLES 6 THROUGH 11

In the same equipment used in Example 1, employing the same procedure as in that Example, additional examples were run as follows:

| Example | Silyated Carborane Substrate | Nucleophile Type | Amount (wt. %) | Phase Transfer Catalyst | Yield (%) |
|---|---|---|---|---|---|
| 6 | Dexsil 202 | KF | 50 | none | 93 |
| 7 | Dexsil 202 | KOH | 10 | Adogen 464 | 93 |
| 8 | Dexsil 202 | KOH | 10 | none | 93 |
| 9 | o-C$_2$B$_{10}$H$_{10}$(Si(CH$_3$)$_2$Cl)$_2$ | KF | 10 | Adogen 464 | 91 |
| 10 | p-C$_2$B$_{10}$H$_{10}$(Si(CH$_3$)$_2$OH)$_2$ | KF | 10 | Adogen 464 | 95 |
| 11 | O-C$_2$B$_{10}$H$_{11}$Si(CH$_3$)$_3$ | NaOCH$_3$ | 8 | None | 92 |

What is claimed is:

1. A highly selective method for cleaving a carboranyl carbon-silicon bond in a substrate having at least one of such bonds, without cleaving the carborane ring structure, which comprises contacting said substrate with a catalytic amount of a nucleophilic cleavage agent capable of cleaving said bond.

2. A method according to claim 1, wherein said nucleophilic cleavage agent is potassium fluoride.

3. A method according to claim 1, wherein said nucleophilic cleavage agent is potassium hydroxide.

4. A method according to claim 1, wherein said substrate is a carborane-siloxane polymer.

5. A method according to claim 1, wherein said substrate is a monomeric silylated carborane or a derivative thereof.

6. A method according to claim 1, wherein said substrate is a cross-linked carborane-siloxane polymer.

7. A method according to claim 1, wherein said substrate is a cured and compounded elastomeric carborane-siloxane polymer.

8. A method according to claim 1, wherein said substrate is a shaped article formed of a carborane-siloxane polymer.

9. A method according to claim 1, further including the steps of adding a proton source and recovering the carborane compound.

10. A method according to claim 9, wherein said carborane is meta-carborane.

11. A method according to claim 1, wherein said contacting is in an organic solvent or water.

12. A method according to claim 11, further including the step of adding a phase transfer catalyst selected from the group consisting of cationic, anionic or nonionic surface active agents to said solvent.

13. A method according to claim 11, further including the step of adding a crown ether to said solvent.

14. A method for preparing meta-carborane in bulk from a silylated derivative of ortho-carborane comprising isomerizing said ortho-carborane silylated derivative to the corresponding meta-carborane silylated derivative, cleaving the carboranyl carbon-silicon bonds of said meta-carborane silylated derivative by contacting said derivative with a catalytic amount of a nucleophilic cleavage agent capable of cleaving said bonds without degrading the carborane ring structure, in the presence of a source of proton hydrogen to produce meta-carborane, and recovering said meta-carborane.

15. A method according to claim 14, wherein said silylated derivative of ortho-carborane is a trialkylsilylo-carborane.

16. A method according to claim 14, wherein said isomerization comprises heating said silylated derivative of ortho-carborane at a temperature of from about 290° to about 375° C.

17. A method according to claim 14, wherein said nucleophilic cleavage agent is potassium fluoride.

18. A method according to claim 14, wherein said nucleophilic cleavage agent is potassium hydroxide.

19. A method according to claim 14, wherein said contacting is in an inert organic solvent or water.

20. A method according to claim 19, further including the step of adding a phase transfer catalyst selected from the group consisting of cationic, anionic or nonionic surface active agents to said solvent.

21. A method according to claim 19, further including the step of adding a crown ether to said solvent.

* * * * *